(12) United States Patent
Schauer et al.

(10) Patent No.: US 8,725,265 B2
(45) Date of Patent: May 13, 2014

(54) MUSCLE STIMULATOR AND CONTROL METHODS THEREFOR

(71) Applicant: Contour Technology LLC, Minneapolis, MN (US)

(72) Inventors: Anthony Schauer, Hudson, WI (US); Kenneth E. Broen, Birchwood, MN (US); Peter Wollenzien, River Falls, WI (US)

(73) Assignee: Contour Technology, LLC, Minneapolis, MN (US)

( * ) Notice: Subject to any disclaimer, the term of this patent is extended or adjusted under 35 U.S.C. 154(b) by 0 days.

(21) Appl. No.: 13/866,364

(22) Filed: Apr. 19, 2013

(65) Prior Publication Data

US 2013/0296968 A1 Nov. 7, 2013

Related U.S. Application Data

(62) Division of application No. 13/021,378, filed on Feb. 4, 2011, now Pat. No. 8,428,736.

(51) Int. Cl.
*A61N 1/22* (2006.01)
(52) U.S. Cl.
USPC .......................................................... 607/48
(58) Field of Classification Search
USPC ............................................... 607/46, 48, 62
See application file for complete search history.

(56) References Cited

U.S. PATENT DOCUMENTS

| 4,622,973 | A | 11/1986 | Agarwala |
| 4,712,558 | A | 12/1987 | Kidd et al. |
| 5,019,788 | A | 5/1991 | Fischer et al. |
| 5,070,873 | A | * 12/1991 | Graupe et al. ............... 607/48 |
| 5,350,415 | A | 9/1994 | Cywinski |
| 5,643,331 | A | 7/1997 | Katz |
| 6,839,594 | B2 | 1/2005 | Cohen et al. |
| 6,959,216 | B2 | 10/2005 | Faghri |
| 7,280,871 | B2 | 10/2007 | Davis et al. |
| 7,280,873 | B2 | 10/2007 | Freed et al. |
| 7,593,776 | B2 | 9/2009 | Loeb et al. |
| 2006/0200207 | A1 | 9/2006 | Thrope et al. |
| 2007/0106343 | A1 | 5/2007 | Monogue et al. |
| 2008/0208288 | A1 | 8/2008 | Gesotti |
| 2008/0288020 | A1 | 11/2008 | Einav et al. |
| 2009/0118790 | A1 | 5/2009 | Van Herk |
| 2009/0240304 | A1 | 9/2009 | Blum et al. |

* cited by examiner

*Primary Examiner* — George Evanisko
(74) *Attorney, Agent, or Firm* — Leffert Jay & Polglaze, P.A.

(57) ABSTRACT

Apparatus and methods for muscle stimulation and control of muscle stimulators are disclosed. In at least one embodiment, an electrical muscle stimulator includes a belt having a plurality of stimulator pads, a pulse width modulator controlled by a feedback loop, the PWM providing output to control voltages of the stimulator pads, and a control unit to control the PWM and feedback loop. In various embodiments, the control unit monitors PWM output values during a rest phase of a cycle of the muscle stimulator, provides a contraction phase, and following a sag after the contraction phase, uses PWM values from the rest phase to set a voltage for a subsequent rest phase of a next cycle.

8 Claims, 4 Drawing Sheets

MUSCLE STIMULATOR AND CONTROL METHODS THEREFOR

RELATED APPLICATION

This Application is a Divisional of U.S. application Ser. No. 13/021,378, titled "MUSCLE STIMULATOR AND CONTROL METHODS THEREFOR," filed Feb. 4, 2011, (allowed) which is commonly assigned and incorporated herein by reference.

FIELD

The present disclosure relates generally to muscle stimulators, and in particular, in one or more embodiments, the present disclosure relates to control of output of muscle stimulators.

BACKGROUND

Voluntary muscle contraction is controlled by the central nervous system. Voluntary muscle contraction occurs as a result of conscious effort originating in the brain. The brain sends signals, in the form of action potentials, through the nervous system to the motor neuron that innervates several muscle fibers.

Electrical muscle stimulation (EMS), also known as neuromuscular electrical stimulation or electromyostimulation, is the elicitation of muscle contraction using electrical impulses. The impulses are typically generated by a device, and are delivered through electrodes placed on the skin in direct proximity to the muscles to be stimulated. The impulses stimulate motor neurons, causing the muscles to contract. The electrodes are generally gel pads that adhere to the skin. EMS is both a form of electrotherapy and of muscle training.

EMS devices generate electrical impulses that trigger an action potential in muscle nerve fibers (motor neurons). In response to this, the motor neuron produces a response known as a twitch. Twitches performed in succession generated by EMS are the same as a muscle contraction generated by the nervous system in response to regular exercise. The work performed by the muscle fibers varies according to the frequency of the electrical stimulation. For example, 10 impulses per second produces low excitement of fibers, and 120 impulses per second produces high working power in fibers. At the end of contraction muscles relax and return to their original state.

Muscle stimulators use voltage controllers to place a voltage on a stimulator pad affixed to a user's skin to provide a series of pulses at a specific voltage, for a specific period of time, and at a specific frequency, to control rest and contraction of muscles. A pulse width modulation (PWM) scheme may be used to provide outputs to the stimulator pads. However, transitions between a rest phase and a contraction phase, or between a contraction phase and a rest phase, can have, like many electrical signals, an oscillation about the desired voltage when a transition is abrupt. In a muscle stimulator, such oscillation can induce unwanted muscle contraction, or increase discomfort in the user, due to the fluctuations and their effect on muscles.

For reasons such as those stated above, and for other reasons, such as those stated below, which will become apparent to those skilled in the art upon reading and understanding the present specification, there is a need in the art for, among other things, increased control of the operation of muscle stimulators.

DETAILED DESCRIPTION

Figure 1:
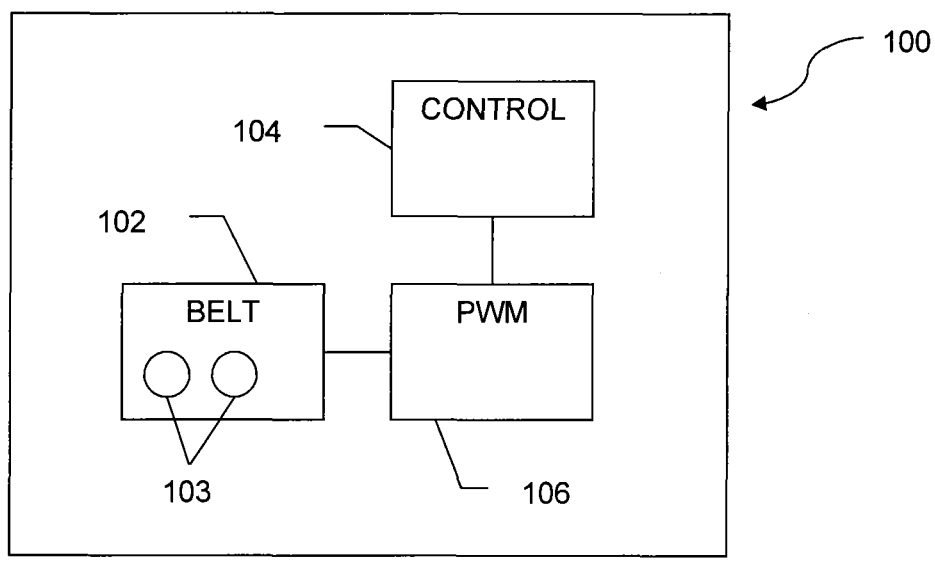
FIG. 1 is a block diagram of a muscle stimulator according to one embodiment of the present disclosure.

In the following detailed description of the embodiments, reference is made to the accompanying drawings that form a part hereof. In the drawings, like numerals describe substantially similar components throughout the several views. These embodiments are described in sufficient detail to enable those skilled in the art to practice the invention. Other embodiments may be utilized and structural, logical, and electrical changes may be made without departing from the scope of the present invention.

The following detailed description is, therefore, not to be taken in a limiting sense, and the scope of the present disclosure is defined only by the appended claims, along with the full scope of equivalents to which such claims are entitled.

Features of muscle stimulators, such as those described herein, can include multiple workout programs, display options, storage for workout programs, data interfaces, and the like. For example, specific features may include by way of example only and not by way of limitations, digital switch inputs; segmented display of program selection, level selection, intensity, elapsed time, paused indication, remaining battery capacity, workout information and test information; waveform control digital outputs (two channels) for delivery of muscle stimulation signals; EEPROM storage for operations information and an error log; and a data interface (such as an RS-232 Serial Interface or the like) for test, error log inspection, operations information inspection and version reporting.

Muscle stimulators such as those in the various embodiments of the present disclosure are typically used for stimulation of healthy muscles in order to enhance and facilitate improved muscle performance. A basic block diagram of a muscle stimulator 100 is shown in FIG. 1. Muscle stimulator 100 comprises in one embodiment a belt or other element 102 for placing stimulator pads 103 in position on a body of a user. As part of the belt, or in a separate element, the muscle stimulator also has a control unit 104, and a pulse width modulator (PWM) 106, which may be part of the control unit in other embodiments. The control unit, PWM, and belt are in one embodiment implemented with a feedback loop such as a proportional integral (PI) loop, or the like. The PI loop has in one embodiment a number of sets of PI constants, each set of PI constants operable to control the PI loop within a range of frequencies, as will be discussed further below. In its use in the embodiments of the present disclosure the PI loop calculates an error value that is the difference between a measured actual voltage and a desired voltage (also referred to as a setpoint.) The controller attempts to minimize the error by adjusting the process control inputs as is known. PI loops use a series of constants as a starting point for the feedback process.

A workout or exercise cycle typically comprises a rest phase and a contraction phase. The rest phase and contraction phase each have a voltage level and a frequency of pulses. One example of a typical cycle takes up on the order of 7-39 seconds, comprising approximately two to twenty-eight seconds of rest at a certain frequency and voltage level, approximately two to eight seconds of contraction at another frequency and/or voltage level, and transitions between rest and contraction, and between contraction and rest. The transitions involve a decrease of voltage from the respective level, often referred to as a sag, to a level below that of either the rest or contraction voltage. Following a short sag time (on the order of a quarter second), a voltage ramp up between the rest phase and the contraction phase occurs. Typical ramp up times are on the order of two seconds. A short ramp down followed by a sag after the contraction phase is typically followed by a steep jump to the rest voltage. This steep jump is what results in oscillations about the rest voltage, which can cause unpleasant sensations for a user. It should be understood that different regimens of training, relaxation, stimulation, and the like can use different cycle frequencies, cycle times, phase times, ramp-up and sag times, and the like, without departing from the scope of the disclosure.

In typical systems, the voltage sag can drop to approximately 50-60% of the contraction voltage, since it is reacting to the end of the rest phase or the contraction phase, and has only a short time to drop to its sag level. However, it is preferred that the voltage sag to a level of approximately 25% of the contraction voltage. In typical systems, this is not possible because the system reacts to the end of the rest or contraction phase, and simply cannot drop to a sag level as low as is preferred. In one embodiment of the present disclosure, a feed forward system is used. This feed forward system, controlled in one embodiment by the control unit, knows the times at which the rest phase and contraction phase are going to end, and begins the sag promptly upon completion of the phase, as opposed to waiting for a traditional feedback or reacting to a determination that voltage is dropping from the rest phase or contraction phase voltage levels. It is this feed forward operation that allows for the sag level to drop in the present disclosure to levels of approximately 25-40% of the contraction voltage.

Figure 2:
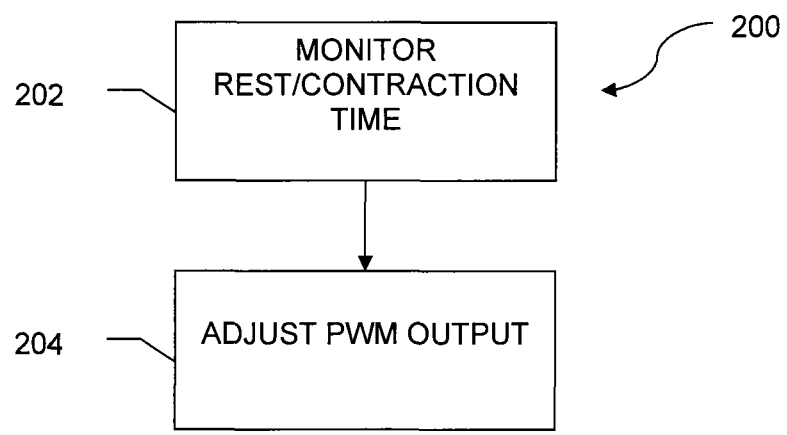
FIG. 2 is a flow chart diagram of a method according to an embodiment of the present disclosure.

The control unit 104 in various embodiments is configured to control operation of the muscle stimulator. A method 200 of forward feedback is shown in flow chart form in FIG. 2. The control unit monitors the time of a rest phase or a contraction phase in block 202, and at an appropriate time (determined by knowing for example the speed at which the PWM signals operate to change PWM output), can automatically adjust the PWM output at block 204, allowing the sag to occur earlier than with a traditional feedback system.

Figure 3:
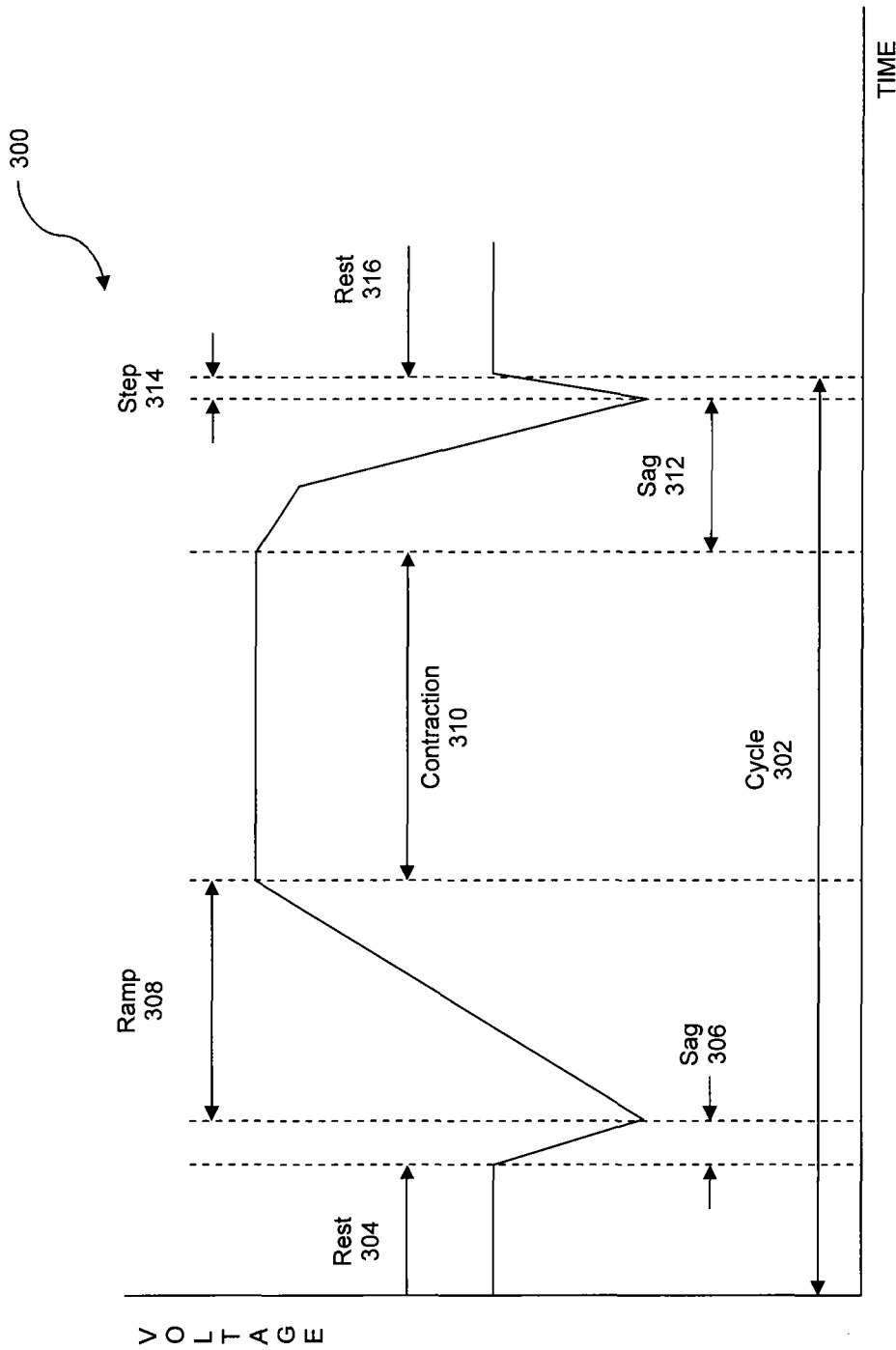
FIG. 3 is a waveform diagram of a cycle according to an embodiment of the present disclosure.

A waveform 300 of a cycle 302 according to one embodiment is shown in greater detail in FIG. 3. In one embodiment, cycle 302 comprises a rest phase 304, a sag from rest 306, a ramp-up 308, a contraction phase 310, a sag from contraction 312, and a near-step (or jump) 314 before rest phase 316 of the next cycle.

Figure 4:
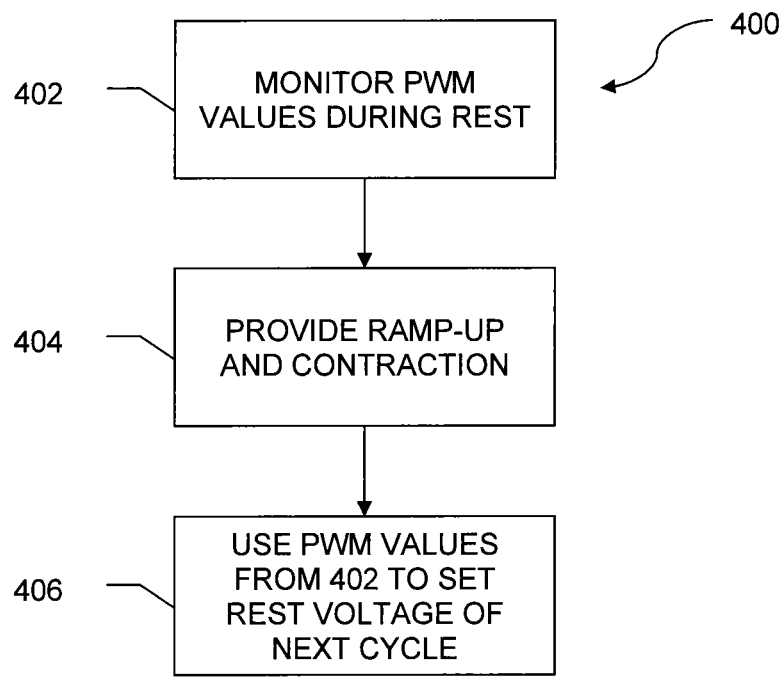
FIG. 4 is a flow chart diagram of a method according to another embodiment of the present disclosure.

In one embodiment shown in FIG. 4 and referring also to FIG. 3, a method 400 comprises monitoring pulse width modulator (PWM) output values during a rest phase 304 of a cycle 302 of the muscle stimulator in block 402, providing a ramp-up 308 and contraction phase 310 in block 404 after a sag 306, and, following a sag 312 after the contraction phase, using the PWM values from the rest phase 304 to set a voltage for a subsequent rest phase 316 of a next cycle in block 406.

The near-step or jump 314 is where oscillations unpleasant to a user can occur, since the near-step is not a ramp but a sudden steep transition from a sag voltage level lower than in typical muscle stimulators to the rest voltage. Further, while a ramp is often used in previous solutions, a ramp-up voltage between contraction and rest can also be unpleasant to a user. A fast transition, and reduced oscillations at the transition, between 314 and 316 are provided in one embodiment of the present disclosure by inserting the PWM values monitored and stored or otherwise saved from a previous rest phase (in this embodiment rest phase 304) into the feedback loop (in one embodiment a PI loop) to force the rest voltage quickly and without oscillation. This is accomplished by using the PWM values that provided stable rest voltage in the previous rest cycle to quickly set the rest level for the next cycle. Advantages to a quick near-step or jump to the rest voltage are that a ramp after contraction and sag can be unpleasant to a user.

In the various embodiments, the PWM is monitored by a feedback loop, and more specifically, in other embodiments, by a PI loop. The PI loop uses constants, as has been discussed above, in the various embodiments to better control the PWM output. As output frequencies in the muscle stimulator are variable typically between 1 Hz to 120 Hz, and the load on the system also increases and decreases as much as 1000 times, a single set of constants is not suitable for all frequency ranges and loads. Each frequency range of a plurality of frequency ranges in one embodiment has its own set of PI constants that provide proper operation of the PWM output control. In one embodiment, each of five frequency ranges has its own set of PI constants, tuned for the range. In this embodiment, the frequency ranges are 1-7 Hz, 8-14 Hz, 15-24 Hz, 25-49 Hz, and ≥50 Hz. It should be understood that more or fewer frequency ranges could be used without departing from the scope of the disclosure.

Figure 5:
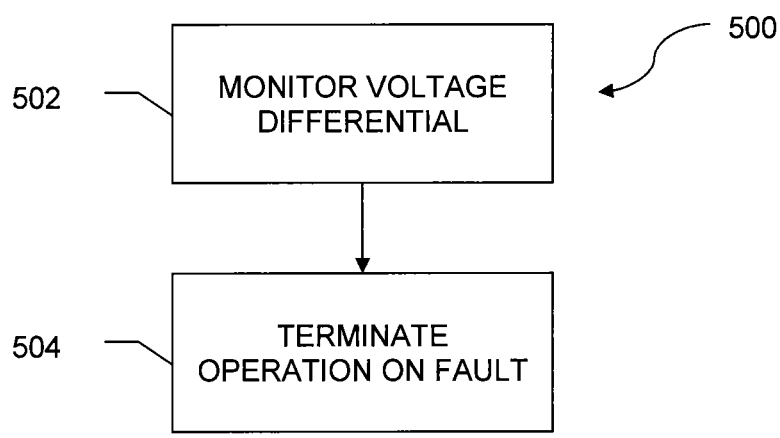
FIG. 5 is a flow chart diagram of a method according to another embodiment of the present disclosure.

In another embodiment, a method 500, shown in flow chart form in FIG. 5, is used for detecting an improper connection of the stimulator pads to a body of a user. If a stimulator pad is not properly affixed to a user, the resultant electrical impulses provided by the muscle stimulator can cause unpleasant sensations, or be ineffective, or could potentially cause other problems. Method 500 comprises monitoring a voltage differential between an actual stimulator voltage from a feedback loop and a desired stimulator voltage in block 502, and terminating operation of the electrical muscle stimulator when the voltage differential exceeds a determined percentage for a determined period of time in block 504. In one example, the determined percentage is approximately thirty percent, and the determined period of time is approximately thirty milliseconds. It should be understood that higher or lower percentages, a more or less time may be used without departing from the scope of the disclosure. Still further, for different workout programs and levels thereof, as well as different voltage levels and the like, different voltages and timing may be used without departing from the scope of the disclosure.

Figure 6:
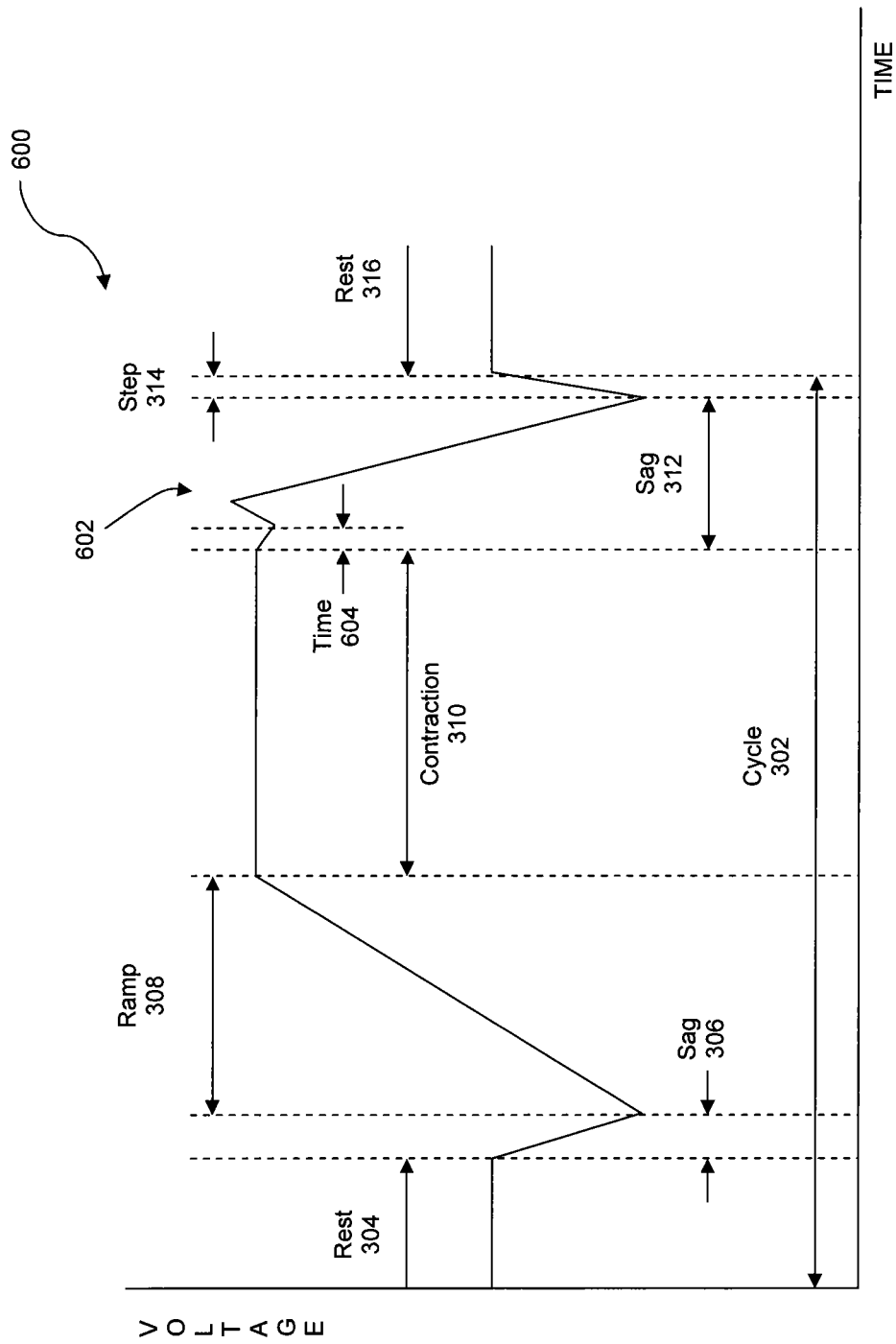
FIG. 6 is a waveform diagram of a cycle according to another embodiment of the present disclosure.

In another embodiment 600 shown in FIG. 6, the presence of an improper connection can be determined using a detection pulse 602 applied during an initial sag period after a contraction pulse. The embodiment of FIG. 6 has a substantially identical waveform for a cycle 302, with the exception of the detection pulse 602. Since for certain programs it may be more difficult to determine the presence of an improper connection, due to timing, voltage levels, or the like, the detection pulse 602, of known size, is applied to the waveform at a particular time increment after the end of the contraction 310. In this embodiment, the time increment is time 604 between the end of contraction 310 and the beginning of detection pulse 602. The monitoring of a voltage differential between an actual stimulator voltage from a feedback loop and a desired stimulator voltage (as described in block 502) is in this embodiment performed when the detection pulse is made, so that the differential is measured against a known voltage.

It should also be understood that the embodiments of FIGS. 1, 2, 4, and 5, and the waveforms of FIGS. 3 and 6, can be modified or combined to form one or more other embodiments without departing from the scope of the disclosure.

Conclusion

Methods and apparatus have been described that control operation of an electric muscle stimulator. In one embodiment, a method includes monitoring pulse width modulator (PWM) output values during a rest phase of a cycle of the muscle stimulator, and using PWM values from the rest phase to set a voltage for a subsequent rest phase of a next cycle. Muscle stimulators using those methods are also described.

Although specific embodiments have been illustrated and described herein, it will be appreciated by those of ordinary skill in the art that any arrangement, which is calculated to achieve the same purpose, may be substituted for the specific embodiment shown. This application is intended to cover any adaptations or variations of the present invention. Therefore, it is manifestly intended that this invention be limited only by the claims and the equivalents thereof.

What is claimed is:

1. An electrical muscle stimulator, comprising:
   a belt having a plurality of stimulator pads;
   a feedback loop;
   a pulse width modulator controlled by the feedback loop, the PWM providing output to control voltages of the stimulator pads, wherein the voltage has a cycle comprising a rest phase, a contraction phase, and a sag after the contraction phase; and
   a control unit to control the PWM and the feedback loop, the control unit configured to perform a method of pulse control for the stimulator pads, the method comprising:
   monitoring PWM output values during the rest phase of the cycle of the muscle stimulator;
   providing the contraction phase; and
   following the sag after the contraction phase, using PWM values from the rest phase to set a voltage for a subsequent rest phase of a next cycle.

2. The muscle stimulator of claim 1, wherein the control unit is configured to provide a first cycle of the muscle stimulator with a voltage following a sag after the rest phase that ramps up over approximately a two second duration to the contraction phase voltage.

3. The muscle stimulator of claim 1, wherein the control unit is further configured to insert PWM values from the rest phase into the feedback loop to set the voltage for the subsequent rest phase of the next cycle.

4. The muscle stimulator of claim 1, wherein the feedback loop is a proportional integral (PI) loop.

5. The muscle stimulator of claim 1, wherein the control unit is further configured to monitor for a connection fault of electrodes of the muscle stimulator, and to terminate operation of the muscle stimulator upon detection of a connection fault.

6. The muscle stimulator of claim 5, wherein the control unit is further configured to monitor for a connection fault by monitoring voltage feedback error in the feedback loop, and terminating operation when a differential between feedback voltage and desired voltage exceeds a determined percentage for a determined period of time.

7. The muscle stimulator of claim 5, wherein the control unit is further configured to measure the differential between the feedback voltage and the desired voltage upon initiation of a detection pulse.

8. The muscle stimulator of claim 5, wherein the control unit is configured to initiate the detection pulse at a determined time within a program of the muscle stimulator.

* * * * *